United States Patent [19]

Rebuffat

[11] Patent Number: 4,605,002

[45] Date of Patent: Aug. 12, 1986

[54] PURSE-STRING INSTRUMENT

[76] Inventor: Carlo Rebuffat, Via Galilei 7, Trento, Italy

[21] Appl. No.: 585,929

[22] Filed: Mar. 5, 1984

[30] Foreign Application Priority Data

Mar. 11, 1983 [IT] Italy ................................ 20033 A/83

[51] Int. Cl.$^4$ ............................................. A61B 17/04
[52] U.S. Cl. ................................ 128/321; 128/334 R; 128/346
[58] Field of Search ............... 128/321, 322, 325, 346, 128/334 R, 334 C

[56] References Cited

U.S. PATENT DOCUMENTS

| | | | |
|---|---|---|---|
| 1,982,209 | 11/1934 | Furniss | 128/346 |
| 2,626,608 | 1/1953 | Garland | 128/346 |
| 3,265,069 | 8/1966 | Healey et al. | 128/334 C |
| 3,916,908 | 11/1975 | Leveen | 128/346 |
| 4,106,508 | 8/1978 | Berlin | 128/346 |
| 4,226,240 | 10/1980 | Walker | 128/321 |
| 4,345,600 | 8/1982 | Rothfuss | 128/346 X |

FOREIGN PATENT DOCUMENTS

| | | | |
|---|---|---|---|
| 708659 | 7/1931 | France | 128/334 R |
| 361792 | 2/1973 | U.S.S.R. | 128/346 |

OTHER PUBLICATIONS

"Arteriosclerotic Aneurysms of the Abdominal Aorta," vol. 137, No. 5, p. 769.
Vezeridis et al, "EEA Stapler in Low Anterior Anastomosis," Disc. Col. & Rect., May–Jun. 1982, pp. 364–367.
"The Surgeon at Work," Foss, Surgery, Gynecology & Obstetrics, vol. 97, No. 2, pp. 248–249, Aug. 1953.
"The Surgical Armamentarium," American V. Mueller, 1980, p. 84.

Primary Examiner—Michael H. Thaler

[57] ABSTRACT

A new purse-string instrument having arc shaped jaws and handles is described, by which it is possible to place mechanically, in surgery, purse-string sutures in very narrow and deep areas of the organism.

1 Claim, 7 Drawing Figures

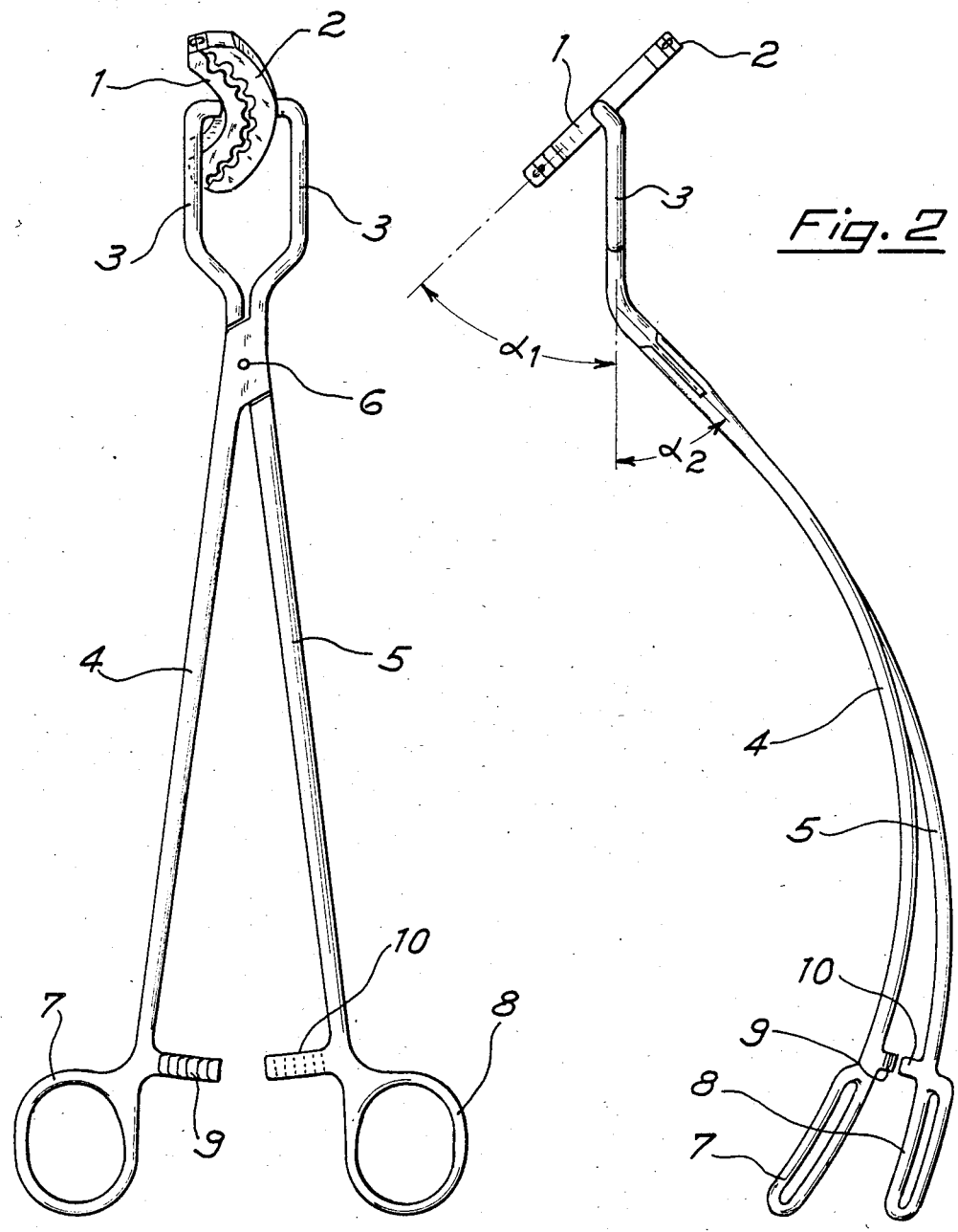

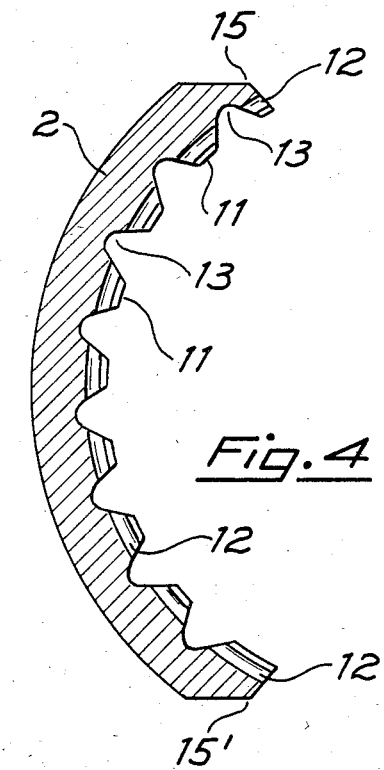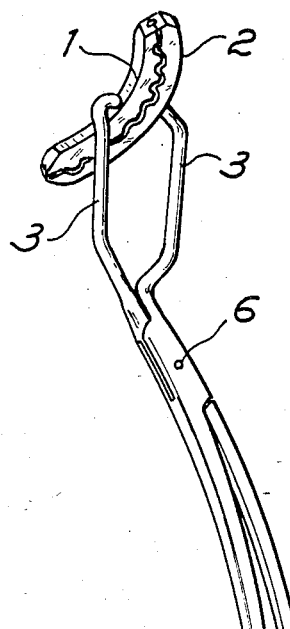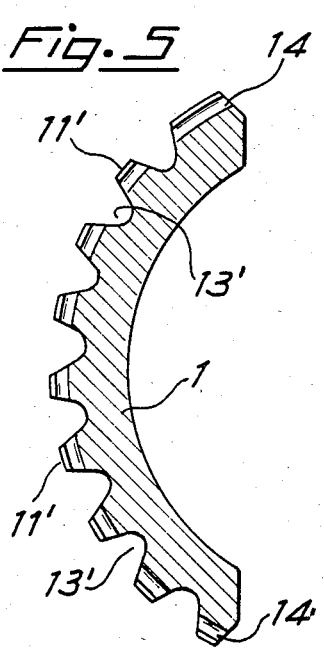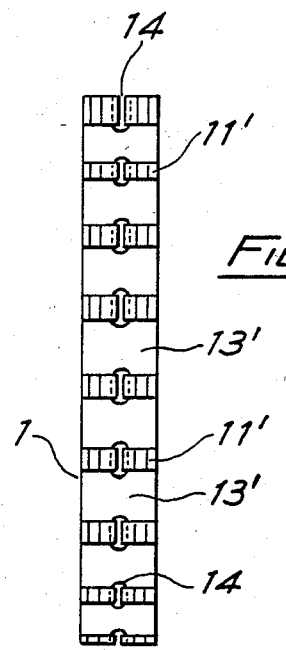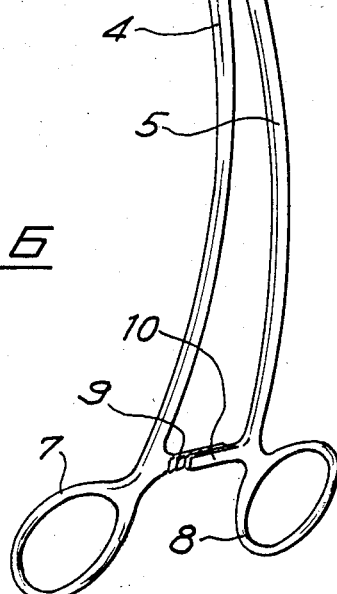

PURSE-STRING INSTRUMENT

BACKGROUND OF THE INVENTION

The recent introduction in surgery of the mechanical circular staple devices which allow the mechanical placement of anastomoses, has made more frequent the requirement of purse-string sutures which are essential in order to suitably utilize said mechanical circular staplers.

Purse-string suture is a type of suture largely placed during surgical operations: its execution except when very narrow and deep areas is involved, is rather simple and quick to be carried out.

Purse-string sutures can be placed manually or mechanically by means of traditional purse-string instruments which all are characterized by having both the two jaws—holding in between the tissure edges where it has to be placed purse-string suture—and the two handles connecting jaw-holders and handle ringed ends, which extend rectilinearly.

Traditional purse-string instruments due to their straight form require for their utilization a space large enough so that they can be fitted end-to-end with the length of the straight needle when inserting the needle into the proper channel of the jaws.

However, should the purse-string suture be placed in difficult technical conditions such as when it has to be placed on organs which lay deep in restricted sites, then traditional purse-string instruments cannot be employed and consequently, the purse-string suture may only be manually carried out, sometimes with great difficulty, and that involves a considerable extension of the operating time as well as a less certainty of execution. Thus, in the digestive apparatus surgery, the placement of the purse-string suture, a procedure which is essential for a successful operation using mechanical circular staplers, may be effected with the purse-string instruments of the art, easily and quickly at the level of the small intestine and colon, while the same suture at the level of the extraperitoneal rectum is practically impossible because the total encumbrance encompassing the jaws of the instrument and the straight needle which must be passed through the proper channel of the jaws is generally bigger than the space at disposal to carry out this maneuver.

SUMMARY OF THE INVENTION

It is the object of the invention to provide a new purse-string instrument having arc shaped jaws as well as arc shaped handles by which it is made possible the mechanical placement of purse-string sutures even in difficult technical conditions, i.e. narrow and deep operating sites.

Particularly the purse-string instrument of the invention, due to the particular shape of its jaws and handles, the latter extending between the jaw-holders and the two ring shaped ends, makes possible the mechanical placement of purse-string sutures even in very narrow and deep operating sites, e.g. at the level of the extraperitoneal rectum, thus sharply reducing operation time and increasing the certainty of the execution.

Compared to the purse-string instruments having straight jaws and handles, the purse-string instrument of the invention although the lateral dimension remain unchanged, allows a remarkable increase in the working surface of its jaws.

A further advantage is gained by the purse-string instrument of the invention, since due to the arc shaped handles it allows a perfect visibility of the operative field.

A further advantage of the purse-string instrument of the invention is represented by the specially curved needle to be fitted end-to-end with the arc shaped jaws, by which it is possible to gain a great reduction of lateral space occupied when inserting them in the proper channels of the arc-shaped jaws.

DETAILED DESCRIPTION OF A PREFERRED EMBODIMENT

The attached drawings are given as non-limiting example of a preferred embodiment of the purse-string instrument according to the present invention.

FIG. 1 is a plan view from above of the purse-string instrument showing the two coaxial arc shaped jaws 1 and 2, which fit together when the purse-string instrument is tightened up and the two intermediate segments 3 and the handles 5 and 4 rigidly connected to the two segments 3 of which they are the continuation but extending curvilinearly, hinged in 6 and having the two rings 8 and 7 at the opposite ends of the jaw 1 and 2 in respect to the hinge 6. The arc shaped handles 5 and 4 carry each proximally to the two ringed ends 7 and 8 notched side segments 9 and 10 suitable for mutual engagement to block the string-purse instrument in the required position.

FIG. 2 is a left side view of the string-purse instrument of FIG. 1. There is exhibited a particular of construction of the preferred embodiment, in which the two angles $\alpha_1$ and $\alpha_2$ are complementary angles. The angle $\alpha_1$ is formed by the projection of the working surface of the jaws 1 and 2 matched and the longitudinal axis of the intermediate segments 3; the second angle $\alpha_2$ is formed by the same longitudinal axis of the intermediate segments 3 and the tangent to the arc shaped handles 4 and 5 at the end of the segments 3. The different bend and length of handles 4 and 5 are also shown.

FIG. 3 is a view of the external jaw 2 from its hollow side, where are shown the parts 11 having smaller radius of curvature, which parts 11 all together form the working surface of the jaw 2 and are longitudinally grooved to provide a safe hold of the tissues and the channel 12 which crosses all the parts 11 for the insertion of the curved needle.

FIG. 4 represents a cross-section of the external jaw 2 where are shown the parts 11, the transversal recess 13 having a U cross-section, the channel 12 and the bluntings 15 and 15' which provide a further reduction of the overall size of the purse-string instrument.

FIG. 5 is a cross-section of the internal jaw 1 where are shown the parts 11', the transversal recesses 13' having a U cross-section, the channel 14 which crosses all the parts 11' for the insertion of the curved needle.

FIG. 6 is a view of the jaw 1 from its convex side where are shown the parts 11' having bigger radius of curvature, which parts 11' all together from the working surface of the jaw 1 and are longitudinally grooved to provide a safe hold of the tissues and the channel 14 which crosses all the parts 11' for the insertion of the suitable needle.

FIG. 7 is a perspective view of the purse-string instrument according to the previous figures.

In use the purse-string instrument of the invention is introduced into the site where the purse-string suture is to be placed; the edges of the tissues are stretched on the jaws which are then tightened together, the purse-string instrument blocked in the suitable position and the specially curved needle the radius of the curve of which adapts perfectly to the radius of the channel in the jaw, is carefully passed through the proper channels of the jaws. Tissues are then resected, the instrument is opened and the purse-string suture is perfectly placed.

What I claim is:

1. A purse-string instrument for the mechanical placement of a distal purse-string comprising two coaxial arc shaped jaws each having a different curvature and each provided with a working surface and an arc shaped channel for the insertion of a proper needle, two hinged arc shaped handles, and two intermediate segments which connect the jaws to the arc shaped handles and each having a longitudinal axis, wherein the angle formed by the projection of the working surface of the jaws and the longitudinal axis of the intermediate segments connecting the jaws and the handles is the complement of the angle formed by the longitudinal axis of the intermediate segments connecting the jaws and the handles and the tangent to the arc handles at the location of attachment between the arc handles and the segments.

* * * * *